United States Patent
Arai et al.

(10) Patent No.: US 10,269,149 B2
(45) Date of Patent: Apr. 23, 2019

(54) TOMOGRAPHIC IMAGE GENERATION DEVICE, RADIOGRAPHY IMAGING SYSTEM, TOMOGRAPHIC IMAGE GENERATION METHOD AND TOMOGRAPHIC IMAGE GENERATION PROGRAM STORAGE MEDIUM

(71) Applicant: FUJIFILM CORPORATION, Minato-ku, Tokyo (JP)

(72) Inventors: Takahisa Arai, Kanagawa (JP); Naokazu Kamiya, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 10 days.

(21) Appl. No.: 15/415,867

(22) Filed: Jan. 26, 2017

(65) Prior Publication Data
US 2017/0243379 A1 Aug. 24, 2017

(30) Foreign Application Priority Data

Feb. 19, 2016 (JP) .................................. 2016-030009

(51) Int. Cl.
*G06K 9/00* (2006.01)
*G06T 11/00* (2006.01)
(Continued)

(52) U.S. Cl.
CPC .......... *G06T 11/006* (2013.01); *A61B 6/025* (2013.01); *A61B 6/502* (2013.01); *A61B 6/5217* (2013.01);
(Continued)

(58) Field of Classification Search
CPC .... G06T 11/006; G06T 11/008; G06T 11/003; G06T 11/005; G06T 7/0012;
(Continued)

(56) References Cited

U.S. PATENT DOCUMENTS

2007/0183564 A1* 8/2007 Li ........................... A61B 6/025
378/22
2007/0242868 A1* 10/2007 Stanton ................ G01N 23/046
382/131
(Continued)

FOREIGN PATENT DOCUMENTS

JP 2007-203046 A 8/2007
JP 2009-268726 A 11/2009
(Continued)

OTHER PUBLICATIONS

English language translation of the following: Office action dated Jan. 8, 2019 from the JPO in a Japanese patent application No. 2016-030009 corresponding to the instant patent application. This office action translation is submitted now in order to supplement the understanding of the cited references which are being disclosed in the instant Information Disclosure Statement.

*Primary Examiner* — Jose L Couso
(74) *Attorney, Agent, or Firm* — Solaris Intellectual Property Group, PLLC

(57) ABSTRACT

A tomographic image generation device includes a projection image acquisition section configured to acquire plural projection images obtained by radiating radiation onto a breast in sequence from plural radiation angles and by performing imaging at each of the plural radiation angles; a mammary gland density acquisition section configured to acquire a mammary gland density of the breast; a derivation section configured to derive a slice thickness that decreases as the mammary gland density acquired by the mammary gland density acquisition section increases; and a generation section configured to generate a tomographic image at the slice thickness derived by the derivation section based on the plural projection images acquired by the projection image acquisition section.

20 Claims, 14 Drawing Sheets

(51) Int. Cl.
*A61B 6/02* (2006.01)
*A61B 6/00* (2006.01)
*G06T 7/00* (2017.01)

(52) U.S. Cl.
CPC .......... *G06T 7/0012* (2013.01); *G06T 7/0016* (2013.01); *G06T 11/005* (2013.01); *G06T 2207/10081* (2013.01); *G06T 2207/30068* (2013.01); *G06T 2207/30096* (2013.01); *G06T 2210/41* (2013.01)

(58) Field of Classification Search
CPC ............. G06T 7/0016; G06T 2211/436; G06T 2211/424; G06T 2211/428; G06T 2211/40; G06T 2210/41; G06T 2207/10112; G06T 2207/30068; G06T 2207/10072; G06T 2207/70076; G06T 2207/70081; G06T 2207/70084; G06T 2207/10101; G06T 2207/10104; G06T 2207/10108; G06T 2207/10116; G06T 2207/30096; A61B 6/025; A61B 6/502; A61B 6/5217; A61B 6/03; A61B 6/465; A61B 6/5211; A61B 6/032; A61B 6/037; A61B 6/02; A61B 6/405; A61B 6/5205; A61B 5/4312; A61B 5/0033; A61B 5/0073; A61B 8/0825; A61B 10/0041; A61B 2090/3735; A61B 2090/376; A61B 2090/3762; G06K 9/00496; G06K 9/3233; G06K 2209/057; G06K 2209/053; G01N 2223/419; G01N 23/046; Y10S 378/901
See application file for complete search history.

(56) References Cited

U.S. PATENT DOCUMENTS

| | | | | |
|---|---|---|---|---|
| 2011/0110576 | A1* | 5/2011 | Kreeger | G16H 50/50 382/132 |
| 2014/0093029 | A1 | 4/2014 | Masumoto et al. | |
| 2014/0198965 | A1* | 7/2014 | Woods | G06K 9/3233 382/131 |
| 2015/0036796 | A1* | 2/2015 | Dornberger | A61B 6/0414 378/37 |
| 2015/0036904 | A1* | 2/2015 | Jerebko | G06T 11/005 382/131 |
| 2017/0200064 | A1* | 7/2017 | Reicher | G06K 9/6267 |
| 2017/0200269 | A1* | 7/2017 | Reicher | G06T 7/0012 |
| 2017/0200270 | A1* | 7/2017 | Reicher | G06F 19/321 |

FOREIGN PATENT DOCUMENTS

| | | |
|---|---|---|
| JP | 2011-125698 A | 6/2011 |
| JP | 2012-061197 A | 3/2012 |
| JP | 2012-135444 A | 7/2012 |
| JP | 2014-068752 A | 4/2014 |

\* cited by examiner

FIG.3
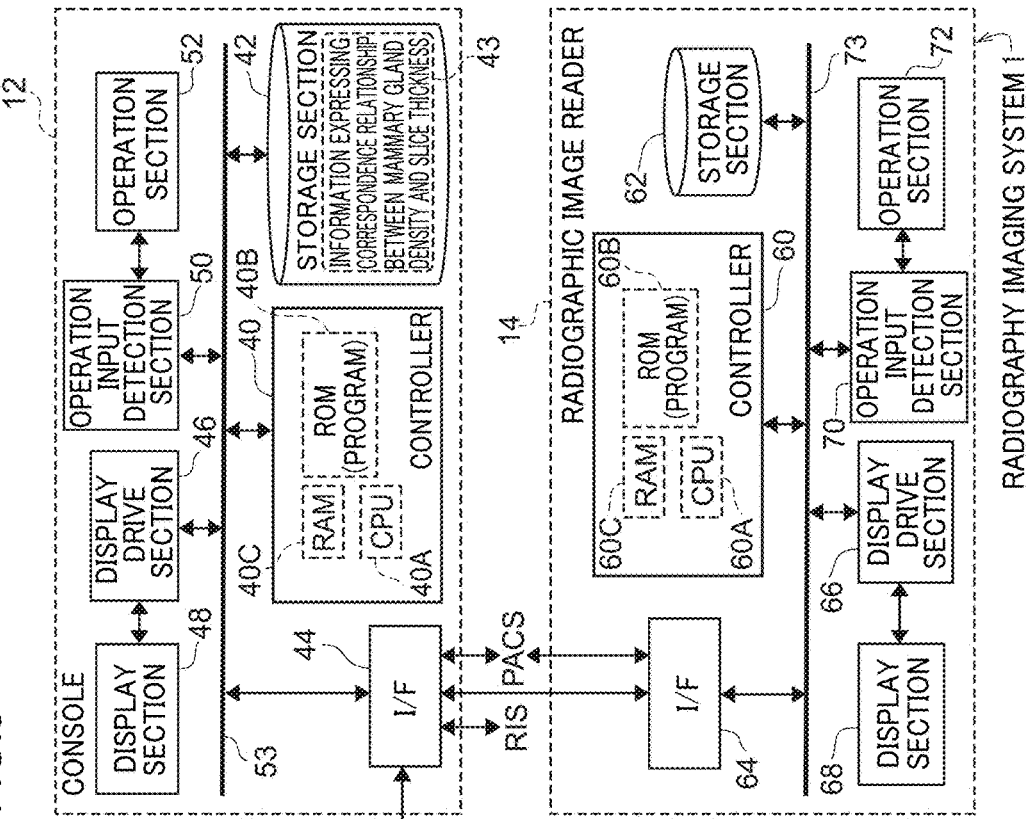
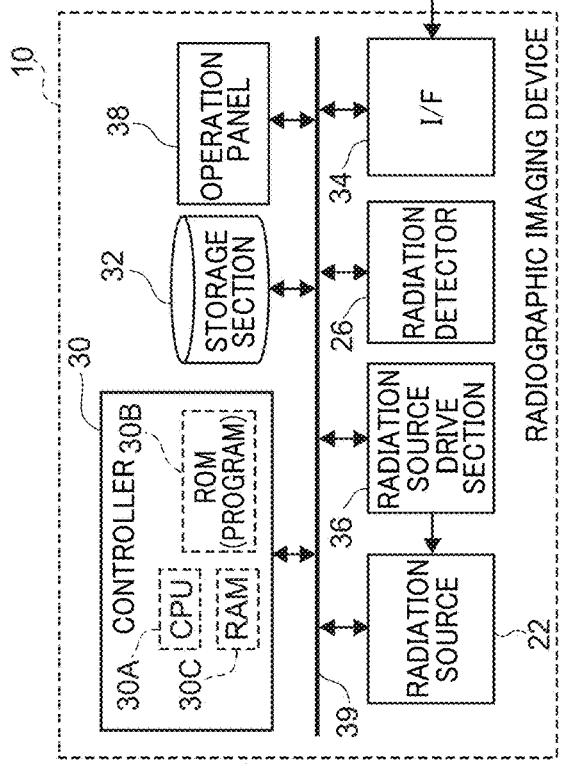

INFORMATION 43 EXPRESSING CORRESPONDENCE
RELATIONSHIP BETWEEN MAMMARY GLAND
DENSITY AND SLICE THICKNESS

INFORMATION 43 EXPRESSING CORRESPONDENCE
RELATIONSHIP BETWEEN MAMMARY GLAND
DENSITY AND SLICE THICKNESS

FIG.9

| MAMMARY GLAND DESITY CLASSIFICATION || SLICE THICKNESS Td (mm) |
|---|---|---|
| BI-RADS | BREAST IMAGING QUALITY CONTROL MANUAL | |
| a. | ALMOST ENTIRELY FAT | 4 |
| b. | SCATTERED FIBROGLANDULAR DENSITY | 2 |
| c. | HETEROGENEOUSLY DENSE | 1 |
| d. | EXTREMELY DENSE | 0.1 |

↑ LOW

MAMMARY GLAND DENSITY

↓ HIGH

INFORMATION 43A EXPRESSING CORRESPONDENCE RELATIONSHIP BETWEEN MAMMARY GLAND DENSITY AND SLICE THICKNESS

TOMOGRAPHIC IMAGE GENERATION DEVICE, RADIOGRAPHY IMAGING SYSTEM, TOMOGRAPHIC IMAGE GENERATION METHOD AND TOMOGRAPHIC IMAGE GENERATION PROGRAM STORAGE MEDIUM

CROSS-REFERENCE TO RELATED APPLICATION

This application claims priority under 35 USC 119 from Japanese Patent Application No. 2016-030009 filed on Feb. 19, 2016, the disclosure of which is incorporated herein by reference in its entirety.

BACKGROUND

Technical Field

The present disclosure relates to a tomographic image generation device, a radiography imaging system, a tomographic image generation method, and a storage medium stored with a tomographic image generation program.

Related Art

Radiographic imaging devices that perform radiographic imaging for the purpose of medical diagnosis and the like are generally known. For such types of radiographic imaging devices, technology is known in which tomosynthesis imaging is performed by radiating radiation onto a subject at different radiation angles, within a specific range, with respect to a detection radiation plane in a radiation detector, and imaging radiographic images (projection images) at each of the radiation angles.

There is also technology for generating tomographic images using plural projection images obtained by tomosynthesis imaging. In such technology, when the slice thickness of the tomosynthesis images is set to a predetermined fixed value, for example, this may result in tomosynthesis images having poor visibility of objects of interest, or may result in tomosynthesis images that do not meet the preferences of the user reading the tomosynthesis images. Technology that addresses this issue by enabling the slice thickness of the tomosynthesis images to be varied is described in Japanese Patent Application Laid-Open (JP-A) No. 2007-203046.

However, generally for a breast as the imaging subject, in cases in which the mammary gland density of a breast is comparatively high, the wider the slice thickness, the higher the possibility that a minute lesion is hidden by a superimposed mammary gland, and the greater the concern that a minute lesion might be overlooked. Moreover, in cases in which the mammary gland density is comparatively low, the thinner the slice thickness, the higher the concern that a lesion might be overlooked due to there being only a small volume of information.

However, in the technology of JP-A No. 2007-203046, there may be a decreased visibility of objects of interest in generated tomosynthesis images due to not considering the mammary gland density of a subject breast.

SUMMARY

In consideration of the above circumstances, the present disclosure provides a tomographic image generation device, a radiography imaging system, a tomographic image generation method, and a storage medium stored with a tomographic image generation program enabling tomosynthesis images to be obtained having high visibility of objects of interest.

A first aspect of the present disclosure is a tomographic image generation device including a projection image acquisition section configured to acquire plural projection images obtained by radiating radiation onto a breast in sequence from plural radiation angles and by performing imaging at each of the plural radiation angles; a mammary gland density acquisition section configured to acquire a mammary gland density of the breast; a derivation section configured to derive a slice thickness that decreases as the mammary gland density acquired by the mammary gland density acquisition section increases; and a generation section configured to generate a tomographic image at the slice thickness derived by the derivation section based on the plural projection images acquired by the projection image acquisition section.

The mammary gland density acquisition section of the tomographic image generation device may be configured to derive the mammary gland density based on the plural projection images acquired by the projection image acquisition section.

The mammary gland density acquisition section of the tomographic image generation device of the above aspect may be configured to acquire as the mammary gland density a mammary gland density classification corresponding to a mammary gland density of the breast.

The mammary gland density acquisition section of the tomographic image generation device of the above aspect may be configured to include a mammary gland density reception section configured to receive information related to mammary gland density, and to acquire a mammary gland density based on the information related to mammary gland density received by the mammary gland density reception section.

The mammary gland density acquisition section of the tomographic image generation device of the above aspect may be configured to derive a predetermined first thickness as the slice thickness either in cases in which the mammary gland density acquired by the mammary gland density acquisition section is a first threshold value or greater, or in cases in which the mammary gland density acquired by the mammary gland density acquisition section exceeds the first threshold value.

The first thickness in such cases may be determined according to a predetermined size of calcification.

The first thickness in such cases may be about 0.1 mm.

The derivation section of the tomographic image generation device of the above aspect may be configured to derive a predetermined second thickness that is larger than the first thickness as the slice thickness either in cases in which the mammary gland density acquired by the mammary gland density acquisition section is, or is less than, a second threshold value that is smaller than the first threshold value, or in cases in which the mammary gland density acquired by the mammary gland density acquisition section is less than the second threshold value.

The second thickness in such cases may be determined according to a predetermined size of tumor.

The second thickness in such cases may be about 4 mm.

In the above aspect, the projection image acquisition section may be configured to acquire plural sets of the plural projection images for the breast of a same subject, the mammary gland density acquisition section may be configured to acquire a mammary gland density based plural projection images of a set selected from the plural sets, and the generation section may be configured to generate a tomographic image for each of the sets at the slice thickness derived by the derivation section.

The plural sets of the plural projection images may include at least one of plural sets of plural projection images corresponding respectively to each of left and right breasts of the same subject, or plural sets of plural projection images of the same breast of the subject imaged at different sessions.

The tomographic image generation device of the above aspect may be configured to further include an information reception section configured to receive information that is one set of information among first information related to a diagnostic objective of diagnosis to be performed using the tomographic image, or second information related to an object of interest to be observed in the tomographic image; and the derivation section may be configured to derive a predetermined slice thickness according to received information irrespective of mammary gland density in cases in which one set of the first or second information has been received by the information reception section.

The derivation section of the tomographic image generation device of the above aspect may be configured to derive the slice thickness based on information expressing a correspondence relationship between the mammary gland density and the slice thickness.

A second aspect of the present disclosure is a radiography imaging system including a radiographic imaging device configured to image plural projection images obtained by radiating radiation onto a breast in sequence from plural radiation angles and imaging at each of the plural radiation angles; and the tomographic image generation device of the first aspect, configured to acquire the plural projection images that have been imaged by the radiographic imaging device and to generate a tomographic image based on the acquired plural projection images.

A third aspect of the present disclosure is a tomographic image generation method including acquiring plural projection images obtained by radiating radiation onto a breast in sequence from plural radiation angles and by performing imaging at each of the plural radiation angles; acquiring a mammary gland density of the breast; deriving a slice thickness that decreases as the acquired mammary gland density increases; and based on the acquired plural projection images, generating a tomographic image at the derived slice thickness.

A fourth aspect of the present disclosure is a non-transitory storage medium storing a program that is executable to cause a computer to perform tomographic image generation processing, the tomographic image generation processing including: acquiring plural projection images obtained by radiating radiation onto a breast in sequence from plural radiation angles and by performing imaging at each of the plural radiation angles; acquiring a mammary gland density of the breast; deriving a slice thickness that decreases as the acquired mammary gland density increases; and based on the acquired plural projection images, generating a tomographic image at the derived slice thickness.

The present disclosure enables the provision of a tomographic image generation device, a radiography imaging system, a tomographic image generation method, and a storage medium stored with a tomographic image generation program enabling tomosynthesis images to be obtained having high visibility of objects of interest.

BRIEF DESCRIPTION OF THE DRAWINGS

Exemplary embodiments will be described in detail based on the following figures, wherein:

FIG. 3 is a block diagram illustrating a configuration of the radiography imaging system of the first exemplary embodiment;

FIG. 9 is a schematic diagram illustrating an example of a correspondence relationship between mammary gland density and slice thickness in a second exemplary embodiment;

DETAILED DESCRIPTION

Detailed explanation follows regarding exemplary embodiments, with reference to the drawings. Note that the present exemplary embodiments do not limit the present disclosure.

First Exemplary Embodiment

Figure 1:
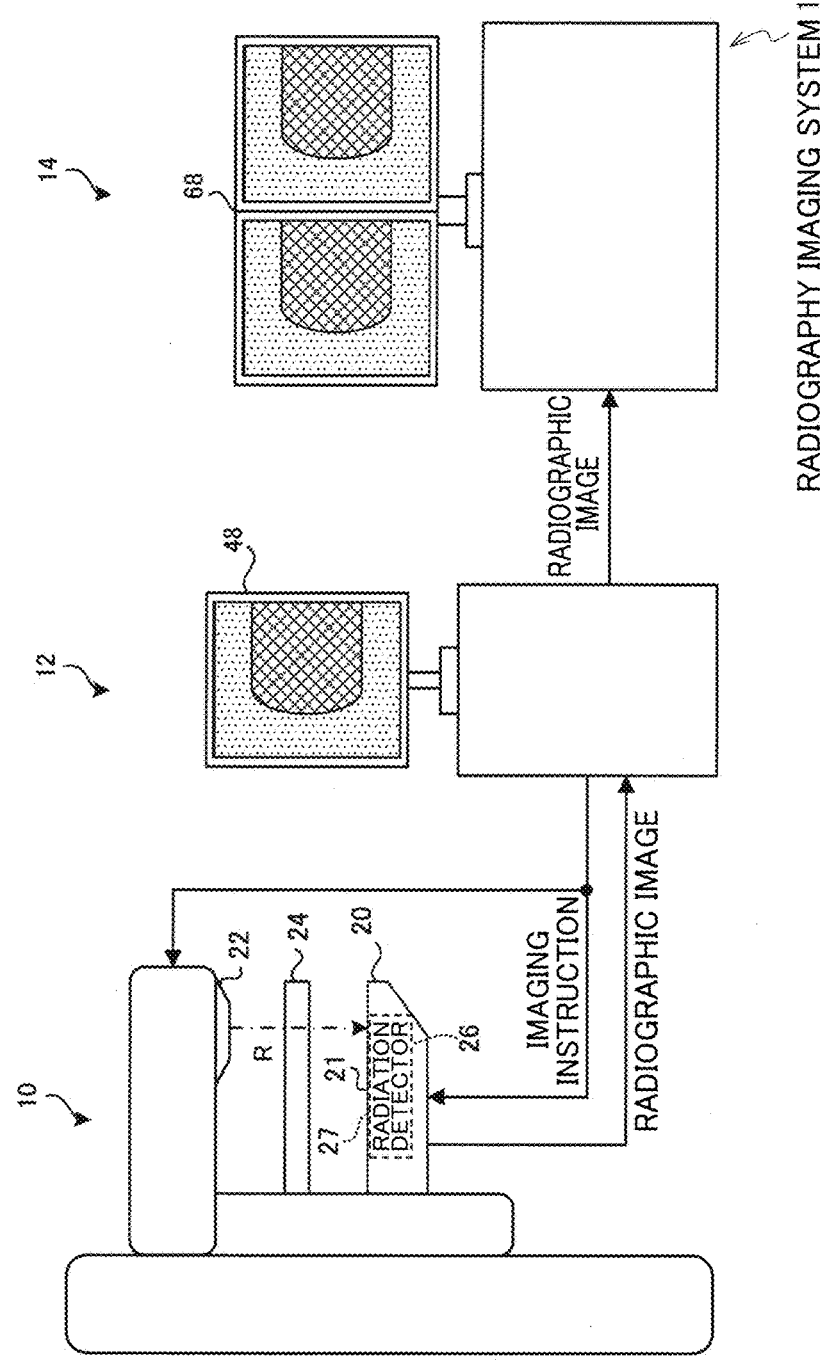
FIG. 1 is a configuration diagram illustrating an overall configuration of a radiography imaging system of a first exemplary embodiment.

Explanation first follows regarding an overall configuration of a radiography imaging system according to the first exemplary embodiment, with reference to FIG. 1.

A radiography imaging system 1 of the present exemplary embodiment includes a radiographic imaging device 10, a console 12, and a radiographic image reader 14. Explanation of the present exemplary embodiment follows regarding a case in which the console 12 functions as an example of a tomographic image generation device.

In the radiography imaging system 1, the radiographic imaging device 10 performs radiographic imaging according to imaging instructed via the console 12.

The radiographic imaging device 10 is a device to image a breast of a subject using radiation R as an imaging subject, with the subject standing in a standing state, or with the subject sitting in an upright seated state on a chair (including a wheelchair) or the like. A specific example of the radiographic imaging device 10 includes a mammography machine.

The radiographic imaging device 10 includes an imaging table 20 provided at an upper face thereof with an imaging face 21 contacted by a breast N of the subject, a radiation source 22, and a press plate 24.

The imaging face 21 is, for example, formed from a carbon composite from the perspectives of transmissivity to the radiation R and strength. A radiation detector 26 is disposed inside the imaging table 20 for detecting radiation R that has passed through the breast and the imaging face 21. A radiographic image is generated based on the radiation R detected by the radiation detector 26. There are no particular limitations to the type of the radiation detector 26 of the present exemplary embodiment, and, for example, an indirect conversion type of radiation detector may be employed that converts radiation R into light and then converts the converted light into charge, or a direct conversion type of radiation detector may be employed that converts the radiation R directly into charge.

In the radiographic imaging device 10, the radiation source 22 is provided facing toward the imaging face 21 of the imaging table 20, and the radiation source 22 emits the radiation R toward the imaging face 21.

In order to perform radiographic imaging of the breast of the subject, the imaging subject of one of the breasts is fixed by the press plate 24, provided between the radiation source 22 and the imaging face 21 of the imaging table 20, pressing the breast against the imaging face 21, and the radiation R is then radiated from the radiation source 22 toward the fixed breast. The press plate 24 employs a material that is transparent to the radiation R.

Figure 2:
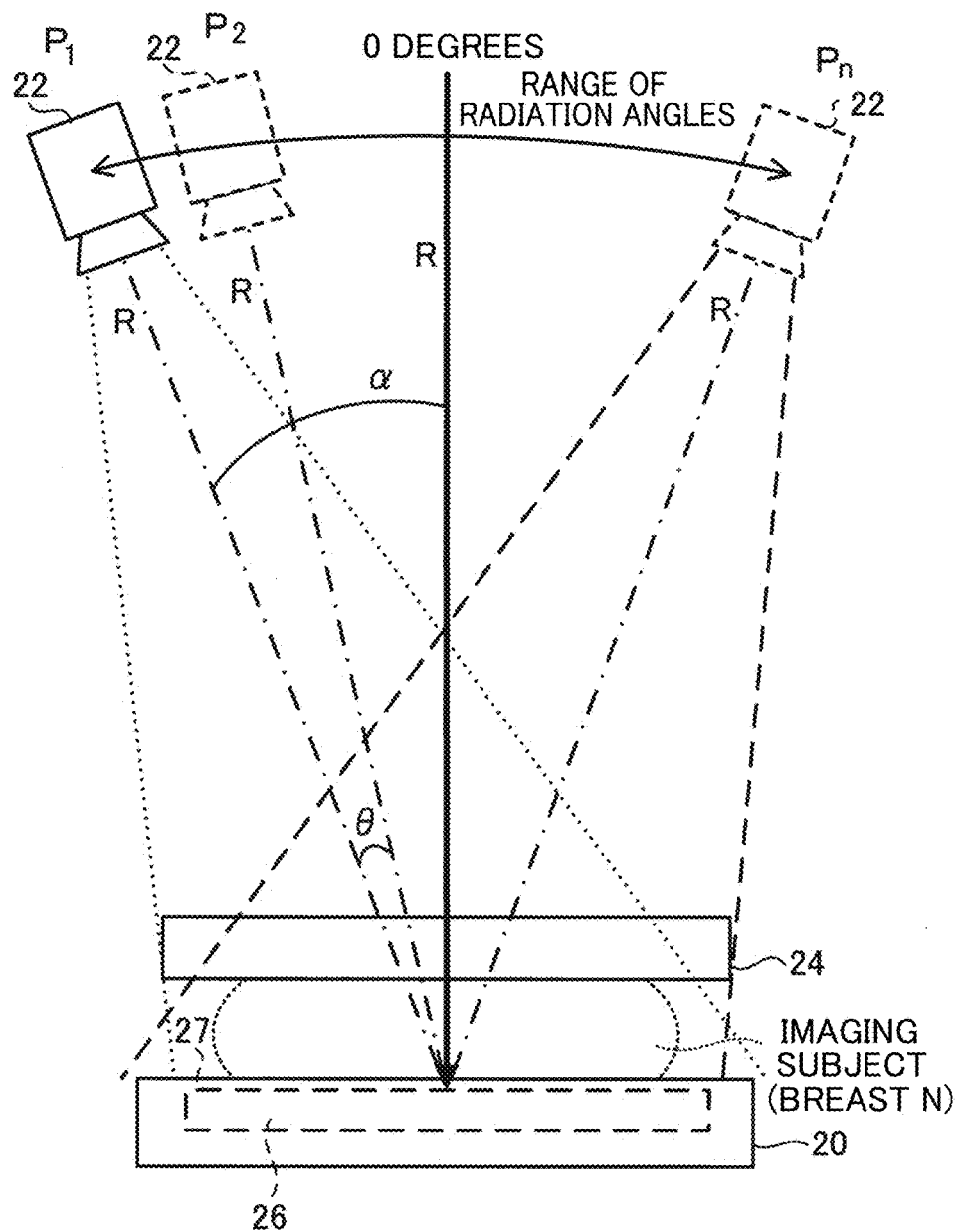
FIG. 2 is a diagram to explain tomosynthesis imaging in a radiographic imaging device of the first exemplary embodiment.

As illustrated in FIG. 2, the radiographic imaging device 10 of the present exemplary embodiment is capable of performing imaging by radiating the radiation R from the radiation source 22 toward the breast N, at different radiation angles of the radiation R within a specific range, and imaging at each of the different incident radiation angles (this being referred to as tomosynthesis imaging). The "radiation angle" is the angle formed between a normal line to a detection plane 27 of the radiation detector 26 and the radiation axis. Hence the radiation angle is 0 degrees when the normal line coincides with the radiation axis. In this example, the detection plane 27 of the radiation detector 26 is a plane substantially parallel to the imaging face 21. Specific examples of ranges of different radiation angles in a single cycle of tomosynthesis imaging are ranges such as ±10 degrees and ±20 degrees to a normal line to the detection plane 27 of the radiation detector 26. Each of the radiographic images imaged at a radiation position corresponding to the respective radiation angle in the tomosynthesis imaging is referred to as a "projection image". The projection images, tomographic images, and the like imaged by the radiographic imaging device 10 are referred to collectively simply as "radiographic images".

In the present exemplary embodiment, as illustrated in FIG. 2, the radiation source 22 is moved from an angle where the radiation angle of the radiation R is an angle α, in sequence to radiation positions where the radiation angle decreases in steps of a specific angle θ, and imaging is performed with the radiation source 22 at n radiation positions from position $P_1$ to position $P_n$.

In the present exemplary embodiment, radiographic images, such as the projection images imaged by the radiation detector 26 of the radiographic imaging device 10, are transmitted to the console 12. The console 12 in the present exemplary embodiment controls the radiographic imaging device 10 using an imaging menu acquired from an external system (for example, from a radiology information system (RIS)) or the like, such as through a wireless local area network (LAN), and various other information. The console 12 of the present exemplary embodiment exchanges various information with the radiation detector 26 of the radiographic imaging device 10. The console 12 of the present exemplary embodiment generates a tomographic image based on the projection images received from the radiographic imaging device 10, and displays various radiographic images such as the projection images and generated tomographic image on a display section 48. The method of generating the tomographic image is not particularly limited, and a known reconstruction method may be employed as a method for generating the tomographic image. Specific examples of methods for generating a tomographic image include a shift-and-add method, as well as other known computed tomography (CT) reconstruction methods. For example, a typical method of filtered back projection (FBP) may be employed as the CT reconstruction method. An FBP method is a reconstruction method using an extended filtered back projection method in which tomographic scanning is performed of a tomographic image in parallel plane slices as part of cone beam CT scanning. Moreover, the iterative reconstruction method described in JP-A No. 2011-125698 may be employed as the reconstruction method. This iterative reconstruction method is also a reconstruction method using CT; however, similarly to in an FBP method, it may also be applied for reconstruction in tomosynthesis imaging.

Moreover, the console 12 of the present exemplary embodiment also transmits radiographic images and the like, such as the projection images and generated tomographic image received from the radiographic imaging device 10, to the radiographic image reader 14.

The radiographic image reader 14 of the present exemplary embodiment displays the radiographic images and the like received from the console 12 on a display section 68. Specific examples of the radiographic image reader 14 include what is referred to as a viewer, however, there is no particular limitation thereto, and portable information terminal devices, such as tablet devices, smart phones, and personal digital assistants (PDAs) may be employed therefor.

FIG. 3 is block diagram illustrating an example of a configuration of the radiography imaging system 1 according to the present exemplary embodiment.

The radiographic imaging device 10 of the present exemplary embodiment includes, in addition to the radiation source 22 and radiation detector 26 described above, a controller 30, a storage section 32, an interface (I/F) 34, a radiation source drive section 36, and an operation panel 38.

The radiation source 22, the radiation detector 26, the controller 30, the storage section 32, the I/F 34, the radiation source drive section 36, and the operation panel 38 are connected together so as to be capable of exchanging various information with each other through a bus 39, such as a system bus or a control bus.

The controller 30 of the present exemplary embodiment controls the overall operation of the radiographic imaging device 10. The controller 30 of the present exemplary embodiment controls the radiation source 22 and the radiation detector 26 when performing radiographic imaging. The controller 30 of the present exemplary embodiment includes a central processing unit (CPU) 30A, read only memory (ROM) 30B, and random access memory (RAM) 30C. Various programs to be executed by the CPU 30A are pre-stored in the ROM 30B. The RAM 30C temporarily stores various data.

Radiographic images imaged by the radiation detector 26, and various other information is stored in the storage section 32. Specific examples of the storage section 32 include a hard disk drive (HDD) and a solid state drive (SSD).

The I/F 34 performs communication of various information with the console 12 using wireless communication or wired communication.

The radiation source drive section 36 moves the radiation source 22 to the radiation positions corresponding to the radiation angles of the radiation R.

The operation panel 38 receives instructions relating to imaging (such as instructions to press the breast with the press plate 24) from an operator performing radiographic imaging. The operation panel 38 is, for example, provided on the imaging table 20 of the medical imaging device 10. The operation panel 38 may be provided as a touch panel.

The console 12 of the present exemplary embodiment is configured by a server computer. As illustrated in FIG. 3, the console 12 includes, in addition to the above-described display section 48, a controller 40, a storage section 42, an I/F 44, a display drive section 46, an operation input detection section 50, and an operation section 52. The controller 40, the storage section 42, the I/F 44, the display drive section 46, and the operation input detection section 50 are connected together so as to be capable of exchanging various information with each other through a bus 53, such as a system bus or a control bus.

The controller 40 of the present exemplary embodiment controls the overall operation of the console 12. The controller 40 of the present exemplary embodiment includes a CPU 40A, ROM 40B, and RAM 40C. Various programs including a tomographic image generation program, described later, to be executed by the CPU 40A are pre-stored in the ROM 40B. The RAM 40C temporarily stores various data.

Radiographic images imaged by the radiographic imaging device 10 are stored in the storage section 42. Information 43 (described in detail later) expressing a correspondence relationship between mammary gland density and the slice thickness for generating the tomographic image (referred to as the slice thickness) is pre-stored in the storage section 42 of the present exemplary embodiment. Specific examples of the storage section 42 include a HDD and a SSD.

The I/F 44 performs communication of various information with the radiographic imaging device 10, the radiographic image reader 14, and an external system, such as a RIS and a picture archiving and communication system (PACS) using wireless communication or wired communication.

The display section 48 displays various information. The display drive section 46 controls the display of various information on the display section 48.

The operation section 52 is employed by an operator to input instructions and various information related to imaging of radiographic images, including instructions for irradiation of the radiation R. There is no limitation to the present exemplary embodiment, and the instructions to emit the radiation R may be performed by the operator from another device or the like provided with a dedicated radiation irradiation instruction switch.

There are no particular limitations to the operation section 52 and examples thereof include various switches, a touch panel, a touch pen, and a mouse. The operation section 52 and the display section 48 may be integrated together as a touch panel display. The operation input detection section 50 detects the operational state of the operation section 52.

The radiographic image reader 14 of the present exemplary embodiment includes, in addition to the display section 68 described above, a controller 60, a storage section 62, an I/F 64, a display drive section 66, an operation input detection section 70, and an operation section 72. The controller 60, the storage section 62, the I/F 64, the display drive section 66, and the operation input detection section 70 are connected together so as to be capable of exchanging various information with each other through a bus 73, such as a system bus or a control bus.

The controller 60 of the present exemplary embodiment controls the overall operation of the radiographic image reader 14. The controller 60 of the present exemplary embodiment includes a CPU 60A, ROM 60B, and RAM 60C. Various programs to be executed by the CPU 60A are pre-stored in the ROM 60B. The RAM 60C temporarily stores various data.

Radiographic images received from the console 12 and various other information are stored in the storage section 62. Specific examples of the storage section 62 include a HDD and a SSD.

The I/F 64 performs communication of various information with the console 12 and an external system, such as a PACS using wireless communication or wired communication.

The display section 68 displays various information. The display drive section 66 controls the display of the various information on the display section 68.

The operation section 72 is employed by an operator to input instructions related to display of radiographic images and various information and the like.

There are no particular limitations to the operation section 72 and examples thereof include various switches, a touch panel, a touch pen, and a mouse. The operation section 72 and the display section 68 may be integrated together as a touch panel display. The operation input detection section 70 detects the operational state of the operation section 72.

In the present exemplary embodiment, each of various programs to be stored in the controller 30 of the radiographic imaging device 10, the controller 40 of the console 12, and the controller 60 of the radiographic image reader 14, are pre-stored on the ROM (30B, 40B, and 60B) of the controller 30, the controller 40, and the controller 60; however, there is no limitation thereto. Each of the programs may, for example, be stored on a storage medium such as a compact disk read only memory (CD-ROM), a removable disk, or the like, and in a format to then be installed from the storage medium to the ROM (30B, 40B, and 60B). The various programs may also be provided so as to be installed on the ROM (30B, 40B, and 60B) from an external device through a communication line, such as the internet.

Next, explanation follows regarding operation of the radiography imaging system 1 of the present exemplary embodiment in tomosynthesis imaging.

First, tomosynthesis imaging (projection imaging) is performed in the radiographic imaging device 10 of the present exemplary embodiment. In the radiography imaging system 1 of the present exemplary embodiment, in order to initiate execution of tomosynthesis imaging of a breast of a subject, an operator employs the operation section 52 of the console 12 to instruct initiation of tomosynthesis imaging. The instruction input to the operation section 52 to initiate execution of tomosynthesis imaging is detected by the operation input detection section 50, and transmitted through the I/F 44 to the radiographic imaging device 10. The operator also positions the breast of the subject, which is the imaging subject, on the imaging face 21 of the imaging table 20 of the radiographic imaging device 10.

After receipt of an instruction to initiate execution of tomosynthesis imaging from the console 12 through the I/F 34, the radiographic imaging device 10 executes tomosynthesis imaging.

The controller 30 of the radiographic imaging device 10 uses the radiation source drive section 36 to move the radiation source 22 to each of the radiation positions, from radiation position $P_1$ to radiation position $P_n$, and uses the radiation detector 26 to perform projection imaging at each of the radiation positions. The imaged projection images are associated with information indicating corresponding radiation angles (radiation positions), and stored in the storage section 32. Each of the projection images is transmitted to the console 12 via the I/F 34 in a state associated with information indicating the corresponding radiation angle (radiation position). After receipt of the projection images via the I/F 44, the console 12 stores the received information in the storage section 42. There is no particular limitation to the timing at which the projection images are transmitted from the radiographic imaging device 10 to the console 12. For example, all of the projection images may be transmitted from the radiographic imaging device 10 to the console 12 after completing tomosynthesis imaging, or a projection image that has been imaged may be transmitted from the radiographic imaging device 10 to the console 12 every time projection imaging is performed at each of the imaging positions.

In the radiography imaging system 1 of the present exemplary embodiment, the console 12 executes tomographic image generation processing according to instruction performed by the operator through the operation section 52 after a series of projection images (projection images corresponding to all of the radiation positions for a single cycle of tomosynthesis imaging) and their radiation angles have been stored on the storage section 42.

Figure 4:
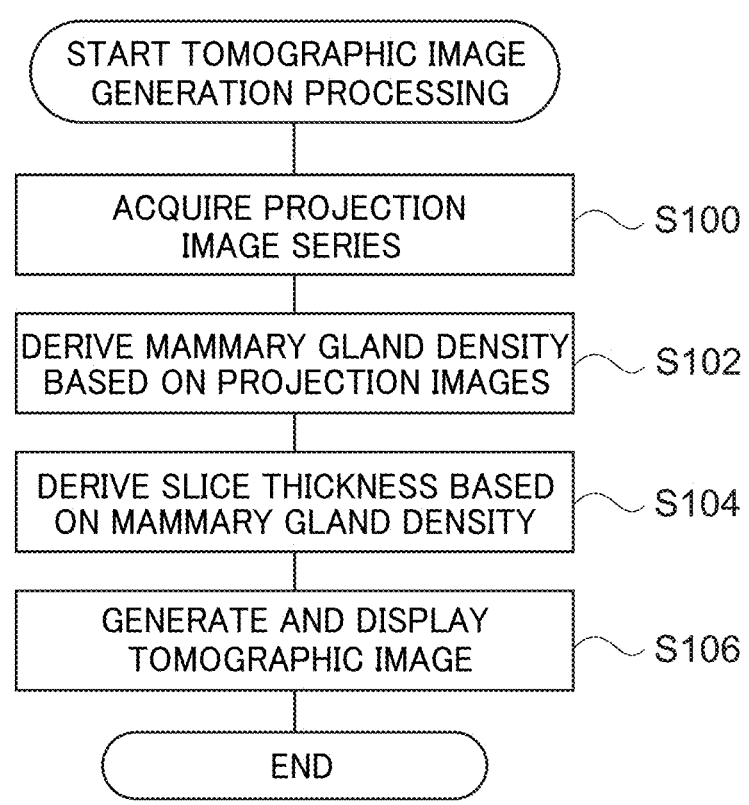
FIG. 4 is a flowchart illustrating tomographic image generation processing executed by a console of the first exemplary embodiment.

FIG. 4 illustrates a flowchart expressing a flow of tomographic image generation processing executed by the controller 40 of the console 12 of the present exemplary embodiment. In the console 12 of the present exemplary embodiment, the tomographic image generation processing illustrated in FIG. 4 is executed by the CPU 40A of the controller 40 executing a tomographic image generation program stored in the ROM 40B.

At step S100 of FIG. 4, the controller 40 acquires the series of projection images subject to processing by reading them from the storage section 42.

At the next step S102, the controller 40 derives the mammary gland density of the breast imaging subject based on the acquired projection images. There are no particular limitations to the method by which the controller 40 derives the mammary gland density based on the projection images. For example, the mammary gland density may be derived based on the total area of white regions (or grey regions) other than the black regions in the projection images. As a specific example, the mammary gland density may be derived from the projection images by the CPU 40A of the controller 40 executing mammary gland density 3D evaluation software such as VOLPARA®. Alternatively, the mammary gland density derivation technology described in JP-A No. 2012-135444 may be applied to by the controller 40 to derive the mammary gland density from the projection images.

The mammary gland density is not derivable from the size of the breast. Moreover, although there is often generally a change in the mammary gland density according to the age of the subject and whether or not the subject has reached menopause, change is not always according to these factors, and there are also differences in the way in which changes occur according to the individual subject. Hence, in the console 12 of the present exemplary embodiment, due to the controller 40 deriving the mammary gland density of the breast imaging subject based on the projection images, an appropriate mammary gland density may be derived without relying on information such as the age of the subject.

Figure 5:
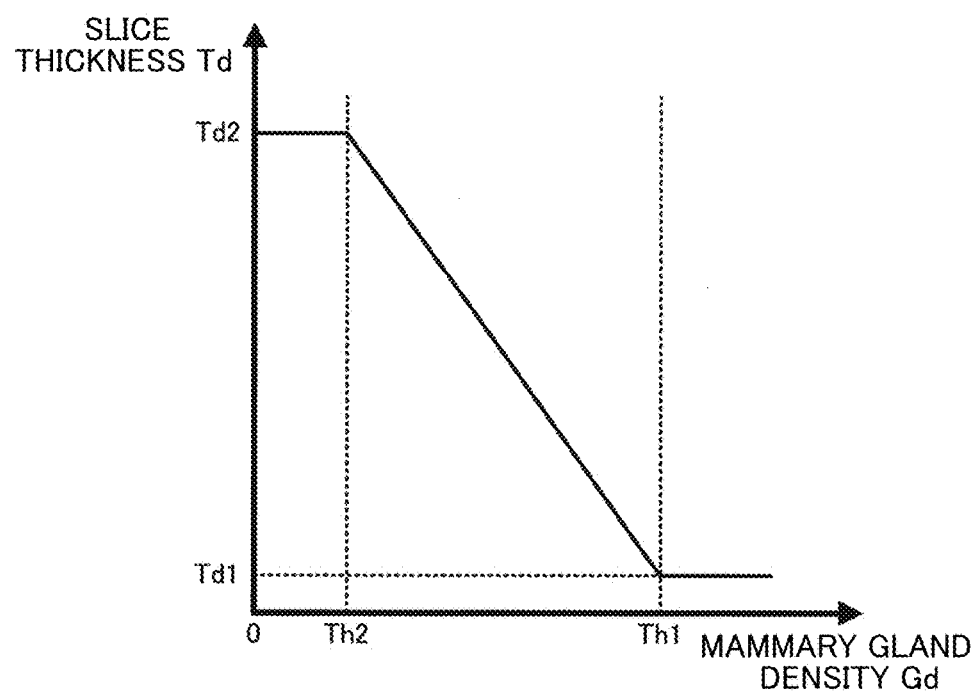
FIG. 5 is a graph illustrating an example of a correspondence relationship between mammary gland density and slice thickness in the first exemplary embodiment.

At the next step S104, the controller 40 derives the slice thickness based on the mammary gland density derived at step S102. In the console 12 of the present exemplary embodiment, the slice thickness corresponding to the mammary gland density is derived based on the information 43 expressing a correspondence relationship between mammary gland density and slice thickness pre-stored in the storage section 42. FIG. 5 is a graph illustrating an example of the information 43 expressing a correspondence relationship between mammary gland density and slice thickness.

Figure 6:
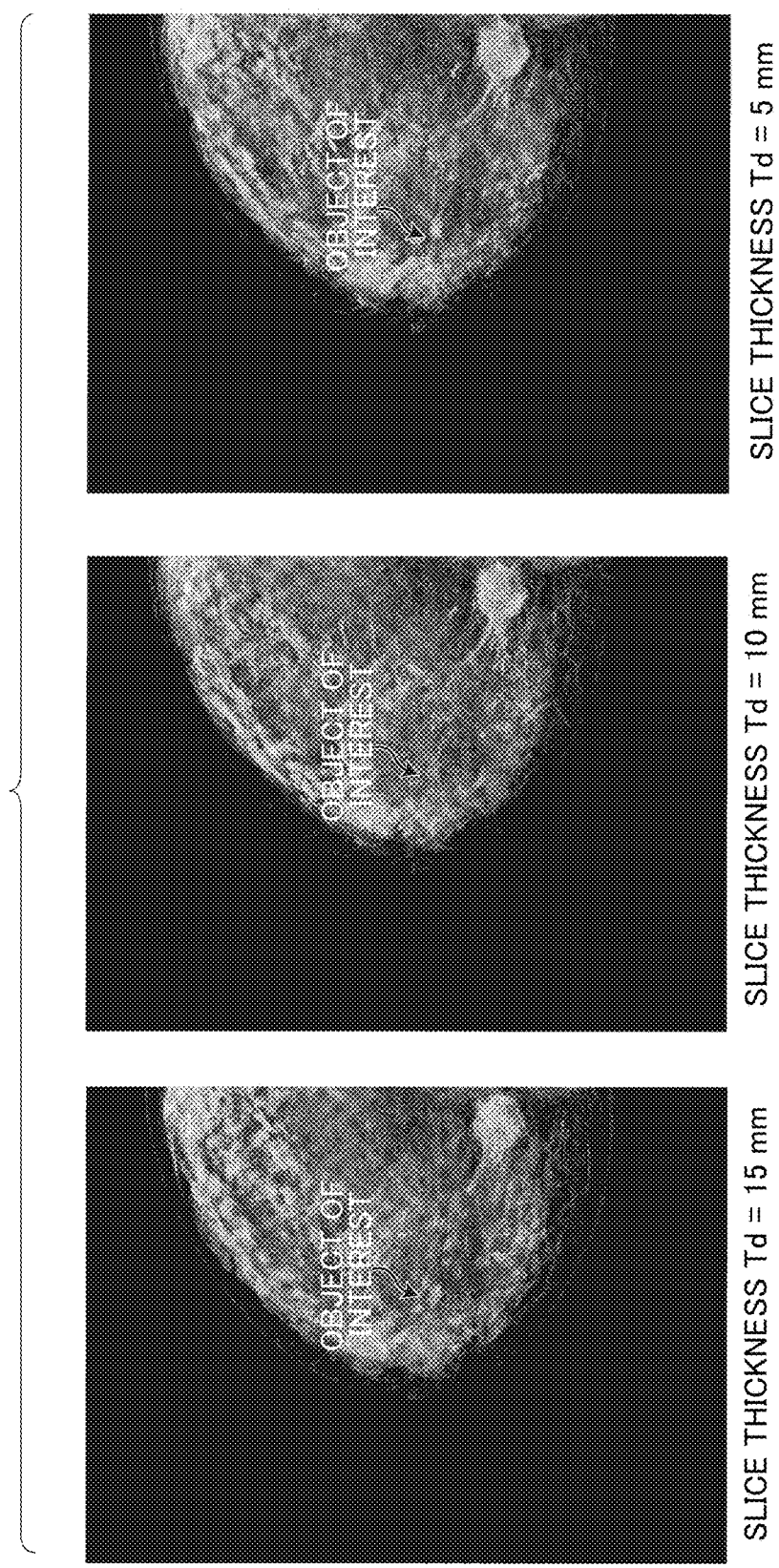
FIG. 6 is a diagram explaining the different appearance (visibility) of an object of interest or the like due to differences in slice thickness.

As illustrated in FIG. 5, a slice thickness Td derived by the controller 40 of the present exemplary embodiment is thinner as a mammary gland density Gd gets higher. Generally, as in the example illustrated in FIG. 6, the appearance (visibility) of an object of interest is different for different slice thicknesses due to the difference in the volume of information included in the generated tomographic image.

Due to the radiation R more readily passing through fat tissue than mammary gland, the mammary gland portions in the radiographic images appear as blank or white colored regions, and fat tissue appears as a dense colored region. The visibility of the object of interest in the tomographic image is accordingly different depending on the mammary gland density Gd. In cases in which the mammary gland density Gd is comparatively high, the greater the slice thickness Td, the higher the possibility that a minute lesion becomes hidden by a superimposed mammary gland, and the greater the concern that a minute lesion might be overlooked. In cases in which the mammary gland density Gd is comparatively low, the thinner the slice thickness, the higher the concern that a lesion might be overlooked due to there being only a small volume of information. The console 12 of the present exemplary embodiment accordingly uses the controller 40 to derive a slice thickness Td of the tomographic image that corresponds to the mammary gland density Gd.

If the slice thickness Td is too thin, then it becomes difficult to see comparatively minute objects of interest, such as calcification. It is accordingly preferable to set a lower limit value for the slice thickness Td. In the present exemplary embodiment, in cases in which the mammary gland density Gd is a threshold value Th1 or greater, a slice thickness Td1 (lower limit value) is derived as the slice thickness Td, irrespective of the actual mammary gland density Gd, as in the information 43 expressing a correspondence relationship between mammary gland density and slice thickness illustrated in FIG. 5. The slice thickness Td1 may be predetermined within the device based on a general size of calcification that needs to be detected, and a specific example thereof is 0.1 mm. The threshold value Th1 corresponds to an example of a first threshold value of the present disclosure.

If the slice thickness Td is too thick, then a comparatively large object of interest, such as a tumor, becomes difficult to see. An upper limit value is accordingly preferably set for the slice thickness Td. In the present exemplary embodiment, in cases in which the mammary gland density Gd is a threshold value Th2 or lower, a slice thickness Td2 (upper limit value) is derived as the slice thickness Td irrespective of actual mammary gland density Gd, as in the information 43 expressing a correspondence relationship between mammary gland density and slice thickness illustrated in FIG. 5. The slice thickness Td2 may be predetermined in the device based on a general size of a tumor that needs to be detected, and a specific example thereof is 4 mm. The threshold value Th2 corresponds to an example of a second threshold value of the present disclosure.

Although, in the present exemplary embodiment, explanation has been given of a case in which the slice thickness Td1 is derived as the slice thickness Td in cases in which the mammary gland density Gd is the threshold value Th1 or greater, irrespective of the actual mammary gland density Gd, the slice thickness Td1 may be derived as the slice thickness Td in cases in which the mammary gland density Gd exceeds the threshold value Th1, irrespective of the actual mammary gland density Gd. Similarly, although, in the present exemplary embodiment, explanation has been given of a case in which the slice thickness Td2 is derived as the slice thickness Td in cases in which the mammary gland density Gd is the threshold value Th2 or less, irrespective of the actual mammary gland density Gd, the slice thickness Td2 may be derived as the slice thickness Td in cases in which the mammary gland density Gd is less than the threshold value Th2, irrespective of the actual mammary gland density Gd.

Due to the controller 40 deriving a slice thickness Td that is thinner the higher the mammary gland density Gd, as illustrated as an example in FIG. 5, the console 12 of the present exemplary embodiment may accordingly generate a tomographic image having high visibility of objects of interest.

After the slice thickness Td has been derived, at the next step S106, the controller 40 uses the tomographic image generation method described above to generate a tomographic image at the derived slice thickness Td based on the acquired projection image series, and, after controlling the display section 48 to display the generated tomographic image, the controller 40 ends the present tomographic image generation processing.

In the present exemplary embodiment, the controller 40 of the console 12 thus derives the mammary gland density Gd of the breast imaging subject based on a projection image series, derives the slice thickness Td corresponding to the derived mammary gland density Gd based on the information 43 expressing a correspondence relationship between mammary gland density and slice thickness such that thinner slice thicknesses Td are associated with higher mammary gland densities Gd, and then generates a tomographic image at the slice thickness Td based on the projection images.

The console 12 of the present exemplary embodiment is accordingly able to obtain tomographic images having high visibility of objects of interest.

Note that the information 43 expressing a correspondence relationship between the mammary gland density and the slice thickness is not limited to that illustrated in FIG. 5. For example, information may be stored that expresses the correspondence relationship described above between the threshold values Th1 and Th2 of the mammary gland density Gd, and the mammary gland density Gd and the slice thickness Td between the threshold values Th1 and Th2.

Figure 7:
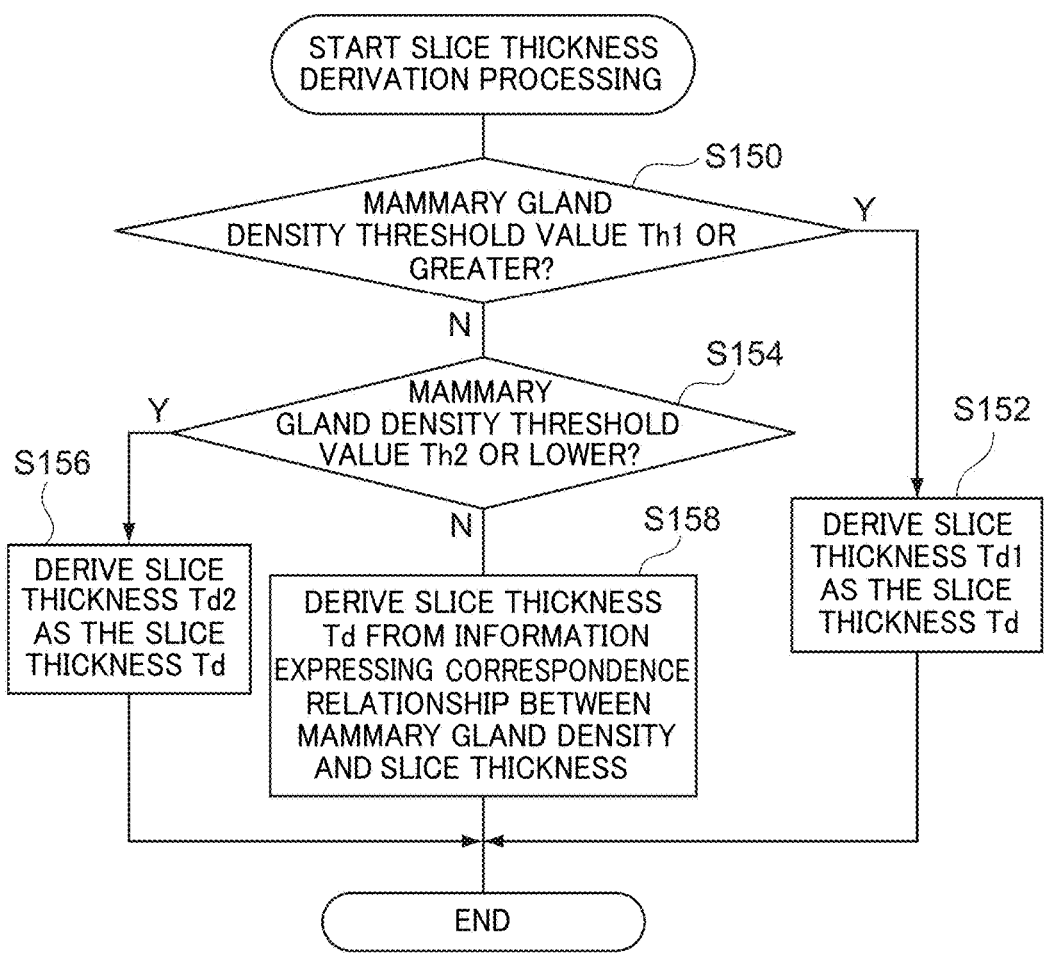
FIG. 7 is flowchart illustrating slice thickness derivation processing executed in image generation processing in cases in which there is a different correspondence relationship between mammary gland density and slice thickness to the correspondence relationship between mammary gland density and slice thickness of FIG. 5.

In such cases, for example, slice thickness derivation processing as illustrated in the example in FIG. 7 may be performed at step S104 of the tomographic image generation processing described above (see FIG. 4).

At step S150 of the slice thickness derivation processing illustrated in FIG. 7, the controller 40 reads the stored threshold value Th1, and determines whether or not the derived mammary gland density is the threshold value Th1 or greater. Affirmative determination is made in cases in which the mammary gland density is the threshold value Th1 or greater, and processing proceeds to step S152. At step S152, the controller 40 derives the slice thickness Td1 as the slice thickness Td, and then ends the present slice thickness derivation processing. However, negative determination is made at step S150 in cases in which the mammary gland density is less than the threshold value Th1, and processing proceeds to step S154.

At step S154, the controller 40 reads the stored threshold value Th2, and determines whether or not the mammary gland density is the threshold value Th2 or lower. Affirmative determination is made in cases in which the mammary gland density is the threshold value Th2 or lower, and processing proceeds to step S156. At step S156, the controller 40 derives the slice thickness Td2 as the slice thickness Td, and then ends the present slice thickness derivation processing.

However, negative determination is made at step S154 in cases in which the mammary gland density exceeds the threshold value Th2, and processing proceeds to step S158. At step S158, the controller 40 derives the slice thickness Td from the information expressing a correspondence relationship between mammary gland density Gd and slice thickness Td, and then ends the present slice thickness derivation processing.

Figure 8:
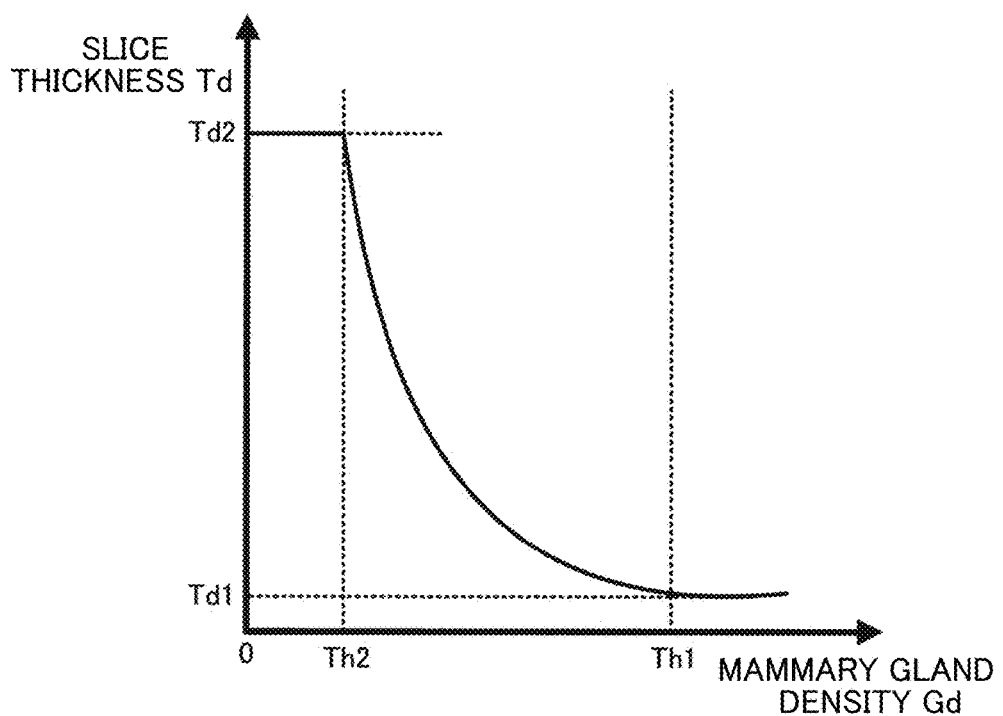
FIG. 8 is a graph illustrating another example of a correspondence relationship between mammary gland density and slice thickness in the first exemplary embodiment.

Although, for example, the correspondence relationship between the mammary gland density Gd and the slice thickness Td is expressed by a linear function (a straight line) as in the graph of FIG. 5, the correspondence relationship between the mammary gland density Gd and the slice thickness Td may be expressed by a quadratic function, an exponential function, or the like (a curve) as in the graph of FIG. 8.

Moreover, a combination may be employed of the information expressing the correspondence relationship between the mammary gland density and the slice thickness illustrated in FIG. 5, and the information expressing the correspondence relationship between the mammary gland density and the slice thickness illustrated in FIG. 8.

Although it is not essential to provide the upper limit value (Td2) and the lower limit value (Td1) for the slice thickness Td that is being derived, the upper limit value (Td2) and the lower limit value (Td1) are preferably provided as in the present exemplary embodiment for the reasons stated above.

Note that the information expressing a correspondence relationship between the mammary gland density Gd and the slice thickness Td should be obtained prior to the console 12 generating the tomographic image, and may, for example, be information that expresses a correspondence relationship between mammary gland density and slice thickness stored in an external storage device or the like, rather than being stored in the storage section 42. Moreover, there are no particular limitations to the method of constructing the information expressing a correspondence relationship between mammary gland density and slice thickness. For example, based on plural sets of projection image series for plural breasts of different mammary gland densities, plural tomographic images may be generated at plural slice thicknesses for each mammary gland density, and the information expressing a correspondence relationship between mammary gland density and slice thickness constructed by deciding on a slice thickness that obtains a desirable tomographic image for each of the respective mammary gland densities.

Second Exemplary Embodiment

Next, explanation follows regarding a second exemplary embodiment. Components similar to the radiography imaging system 1 of the first exemplary embodiment are allocated the same reference numerals, and detailed explanation thereof is omitted.

The configuration of a radiography imaging system 1 is similar to the radiography imaging system 1 of the first exemplary embodiment (see FIG. 1 to FIG. 3), and explanation thereof is omitted.

In the present exemplary embodiment, information expressing a correspondence relationship between mammary gland density and slice thickness differs from that of the first exemplary embodiment, and so explanation follows regarding the information expressing a correspondence relationship between mammary gland density and slice thickness in the present exemplary embodiment. FIG. 9 illustrates an example of information 43A expressing a correspondence relationship between mammary gland density and slice thickness of the present exemplary embodiment.

The information 43A expressing a correspondence relationship between mammary gland density and slice thickness of the present exemplary embodiment is, as illustrated in FIG. 9, information expressing a correspondence relationship between the slice thickness Td and a mammary gland density classification for classifying mammary gland density Gd, rather than the mammary gland density Gd itself. Therefore, although, strictly speaking, the information 43A expressing a correspondence relationship between mammary gland density and slice thickness actually expresses a correspondence relationship between mammary gland density classification and slice thickness Td, for ease of explanation, this is still referred to as "information 43A expressing a correspondence relationship between mammary gland density and slice thickness".

The mammary gland density classification may, for example, employ a classification used by an assessment system in a US Breast Imaging Reporting And Data System (BI-RADS)®. In BI-RADS, mammary gland density is classified into one of four categories (see a. to d. in FIG. 9) according to the level of contrast within the breast region. Alternatively, for example, the mammary gland density classifications from a breast imaging quality control manual may be employed. In a breast imaging quality control manual there are four classifications, "extremely dense", "heterogeneously dense", "scattered fibroglandular density", and "almost entirely fat", in sequence from high to low mammary gland density. Note that in the information 43A expressing a correspondence relationship between mammary gland density and slice thickness illustrated in FIG. 9, for convenience, both the classifications of BI-RADS and the classifications in a breast imaging quality control manual are associated with the slice thickness Td; however, it is sufficient as long as the information 43A expressing a correspondence relationship between mammary gland density and slice thickness associates at least one of the BI-RAD classification or the breast imaging quality control manual classification with the slice thickness Td.

Figure 10:
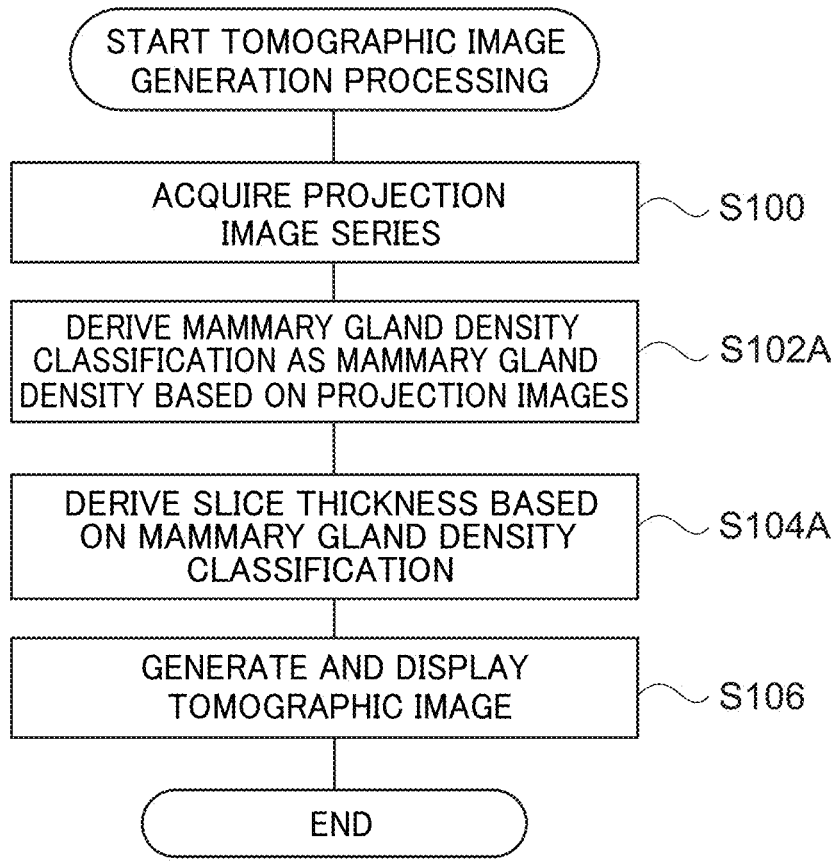
FIG. 10 is a flowchart illustrating a flow of tomographic image generation processing executed by a console of the second exemplary embodiment.

In the tomographic image generation processing executed by the controller 40 of the console 12 of the present exemplary embodiment, as illustrated in FIG. 10, step S102A is executed in place of the step S102 in the tomographic image generation processing of the first exemplary embodiment (see FIG. 4), step S104A is executed in place of the step S104 thereof, and processing is otherwise similar to that of the first exemplary embodiment.

At step S102A, based on the projection images, the controller 40 derives the mammary gland density classification as the mammary gland density. More specifically, the controller 40 derives which applies from the mammary gland density classifications in the information 43A expressing a correspondence relationship between mammary gland density and slice thickness illustrated in FIG. 9.

There are no particular limitations to the method of deriving the mammary gland density classification, and, for example, information expressing a correspondence relationship between mammary gland density Gd and mammary gland density classification may be acquired. Then, the mammary gland density may be derived with a method similar to step S102 of the first exemplary embodiment, and then a mammary gland density classification that corresponds to the derived mammary gland density derived may be derived from the acquired information expressing a correspondence relationship between mammary gland density Gd and mammary gland density classification.

At the next step S104A, the controller 40 derives the slice thickness Td from the information 43A expressing a correspondence relationship between mammary gland density based on the mammary gland density classification and slice thickness.

In such a manner, in the present exemplary embodiment, based on a projection image series, the controller 40 of the console 12 derives a mammary gland density classification as the mammary gland density of the breast imaging subject and, based on the information 43A expressing a predetermined correspondence relationship between mammary gland density and slice thickness such that the slice thickness Td is thinner the higher the mammary gland density Gd, derives the slice thickness Td corresponding to the mammary gland density classification. Then, based on the projection images, the console 12 generates a tomographic image at the slice thickness Td.

The console 12 of the present exemplary embodiment is accordingly also, similarly to in the first exemplary embodiment, able to acquire a tomographic image having high visibility of objects of interest.

Figure 11:
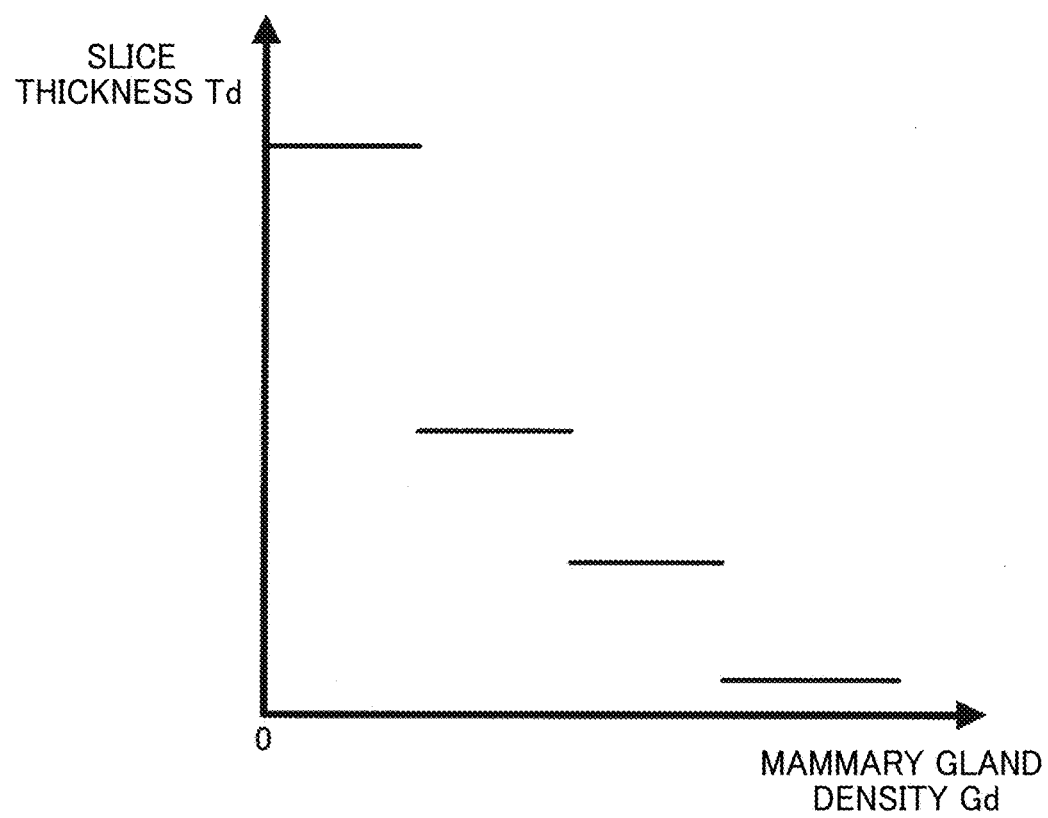
FIG. 11 is a graph illustrating another example of a correspondence relationship between mammary gland density and slice thickness in the second exemplary embodiment.

Obviously, the mammary gland density classification is not limited to those of the examples in the present exemplary embodiment. For example, the mammary gland density classification may be a classification according to the mammary gland density Gd and other information related to mammary gland density (such as the way in which the mammary glands are distributed). Moreover, although in the present exemplary embodiment the information 43A expressing a correspondence relationship between mammary gland density and slice thickness is represented in a table format as illustrated in FIG. 9, the information 43A expressing a correspondence relationship between mammary gland density and slice thickness is not limited to this. For example, similarly to the information 43 expressing a correspondence relationship between mammary gland density and slice thickness in the first exemplary embodiment, by setting a slice thickness Td for each mammary gland density Gd of possible classification ranges for each mammary gland density classification in a graph (schematic diagram) having the mammary gland density Gd on the horizontal axis and the slice thickness Td on the vertical axis, discrete values of slice thickness Td against mammary gland density Gd can be graphed as illustrated in FIG. 11. Such a graph may be employed as the information 43A expressing a correspondence relationship between mammary gland density and slice thickness.

Third Exemplary Embodiment

Next, explanation follows regarding a third exemplary embodiment. Components similar to the radiography imaging systems 1 of the above exemplary embodiments are allocated the same reference numerals, and detailed explanation thereof is omitted.

Configuration of the radiography imaging system 1 is similar to that of the radiography imaging system 1 of the first exemplary embodiment (see FIG. 1 to FIG. 3), and so explanation thereof is omitted.

In the console 12 of the first exemplary embodiment and the second exemplary embodiment, the controller 40 derives the mammary gland density based on the projection images; however, the console 12 of the present exemplary embodiment differs from these exemplary embodiments in the point that a mammary gland density determined by a user based on the projection images is acquired. Part of the tomographic image generation processing performed in the present exemplary embodiment by the controller 40 of the console 12 accordingly differs from that of the first or second exemplary embodiment, and so explanation follows regarding processing that differs. Note that in the following, a person who reads the generated tomographic image and an operator are collectively referred to as the "user".

Figure 12:
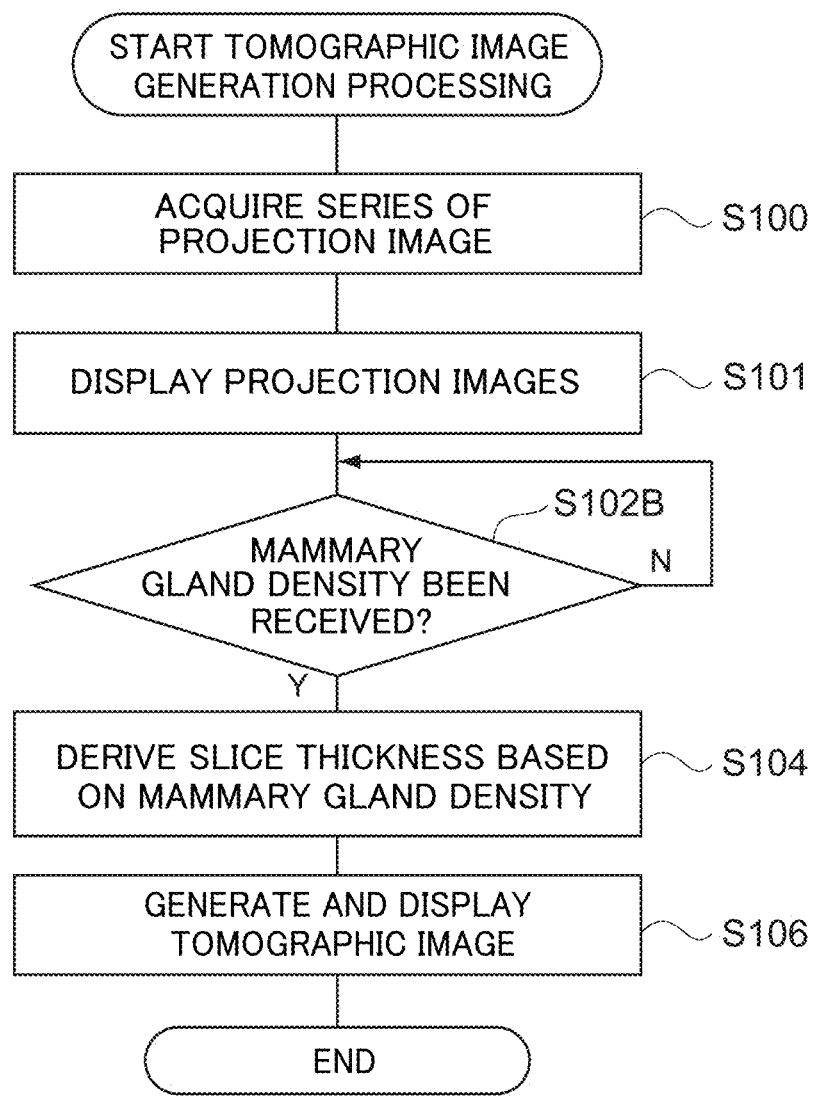
FIG. 12 is a flowchart illustrating a flow of tomographic image generation processing executed by a console of a third exemplary embodiment.

In the tomographic image generation processing executed by the controller 40 of the console 12 in the present exemplary embodiment, as illustrated in FIG. 12, step S101 is executed after step S100 of the tomographic image generation processing of the first exemplary embodiment (see FIG. 4), step S102B is executed in place of step S102 thereof, and processing is otherwise similar to that of the first exemplary embodiment.

At step S101, the controller 40 causes the display section 48 to display the acquired projection images. There is no limitation to the projection images displayed, and the projection images displayed may be all of the acquired projection images, only predetermined projection images, such as projection images imaged at specific radiation angles, or projection images instructed by the user.

The user determines the mammary gland density of the breast imaging subject based on the projection images being displayed on the display section 48. In cases in which, as described in the first exemplary embodiment, the information 43 expressing a correspondence relationship between mammary gland density and slice thickness (see FIG. 5 to FIG. 8) is employed by the controller 40 to derive the slice thickness, the user determines the mammary gland density Gd of the breast (a value of the mammary gland density) itself. However, in cases in which, as described in the second exemplary embodiment, the information 43A expressing a correspondence relationship between mammary gland density and slice thickness (see FIG. 9) is employed by the controller 40 to derive the slice thickness, the user determines the mammary gland density classification that the mammary gland density of the breast should be classified into. In such cases, the categories of mammary gland density classification may be displayed on the display section 48 as information to facilitate the user's determination. There are no particular limitations to the method of determination adopted by the user, and the method may be predetermined. In any case, the result from user's determination is input via the operation section 52 of the console 12.

At the next step S102B, the controller 40 determines whether or not a mammary gland density has been received. In cases in which the operation input detection section 50 has detected input of a user determination result, the controller 40 determines that the mammary gland density has been received. Note that although, as described above, a mammary gland density classification may be received, for ease of explanation this will also be referred to collectively as mammary gland density. Negative determination is made and a standby state is adopted until the mammary gland density is received. However, affirmative determination is made after a mammary gland density has been received, and processing proceeds to step S104.

The controller 40 of the console 12 of the present exemplary embodiment accordingly: acquires the mammary gland density Gd by receiving a determination result in which a user has determined the mammary gland density Gd of the breast imaging subject based on the projection images; derives the slice thickness Td corresponding to the mammary gland density or the mammary gland density classification based on the information 43 or 43A expressing a predetermined correspondence relationship between mammary gland density and slice thickness such that the slice thickness Td is thinner the higher the mammary gland density Gd; and, based on the projection images, generates a tomographic image at the slice thickness Td.

The console 12 of the present exemplary embodiment, similarly to in each of the above exemplary embodiments, is accordingly also able to obtain a tomographic image having high visibility of objects of interest.

Fourth Exemplary Embodiment

Next, explanation follows regarding a fourth exemplary embodiment. Components similar to the radiography imaging system 1 in the above exemplary embodiments are allocated the same reference numerals, and detailed explanation thereof is omitted.

Configuration of the radiography imaging system 1 is similar to that of the radiography imaging system 1 of the first exemplary embodiment (see FIG. 1 to FIG. 3), and so explanation thereof is omitted. In the radiography imaging system 1 of the present exemplary embodiment, the radiographic image reader 14 functions as a tomographic image generation device of the present disclosure.

Explanation has been given above of cases in which the consoles 12 of the first exemplary embodiment and the second exemplary embodiment generate a tomographic image based on a set of a series of projection images. However, explanation follows regarding a case in which there are plural sets of projection image series for the breast of the same subject, and the console 12 of the present exemplary embodiment generates a tomographic image based on each of the sets.

For example, in cases in which diagnosis (screening) is performed for either the left or right breast of the same subject, the tomographic image of one breast may be compared with the tomographic image of the other breast. Moreover, for example, a tomographic image generated based on past projection images may be compared with a tomographic image generated based on current projection images for the same breast of the same subject. In the radiography imaging system 1 of the present exemplary embodiment, when a tomographic image is generated based on plural sets of projection image series for each set in this manner, a tomographic image is generated for each projection image series from plural sets using the slice thickness Td derived based on the set of projection images selected by the user.

In the present exemplary embodiment, the tomographic image generation processing performed by a controller 60 of the radiographic image reader 14 accordingly differs from the tomographic image generation processing performed by the controller 40 of the console 12 of the first exemplary embodiment (see FIG. 4).

Figure 13:
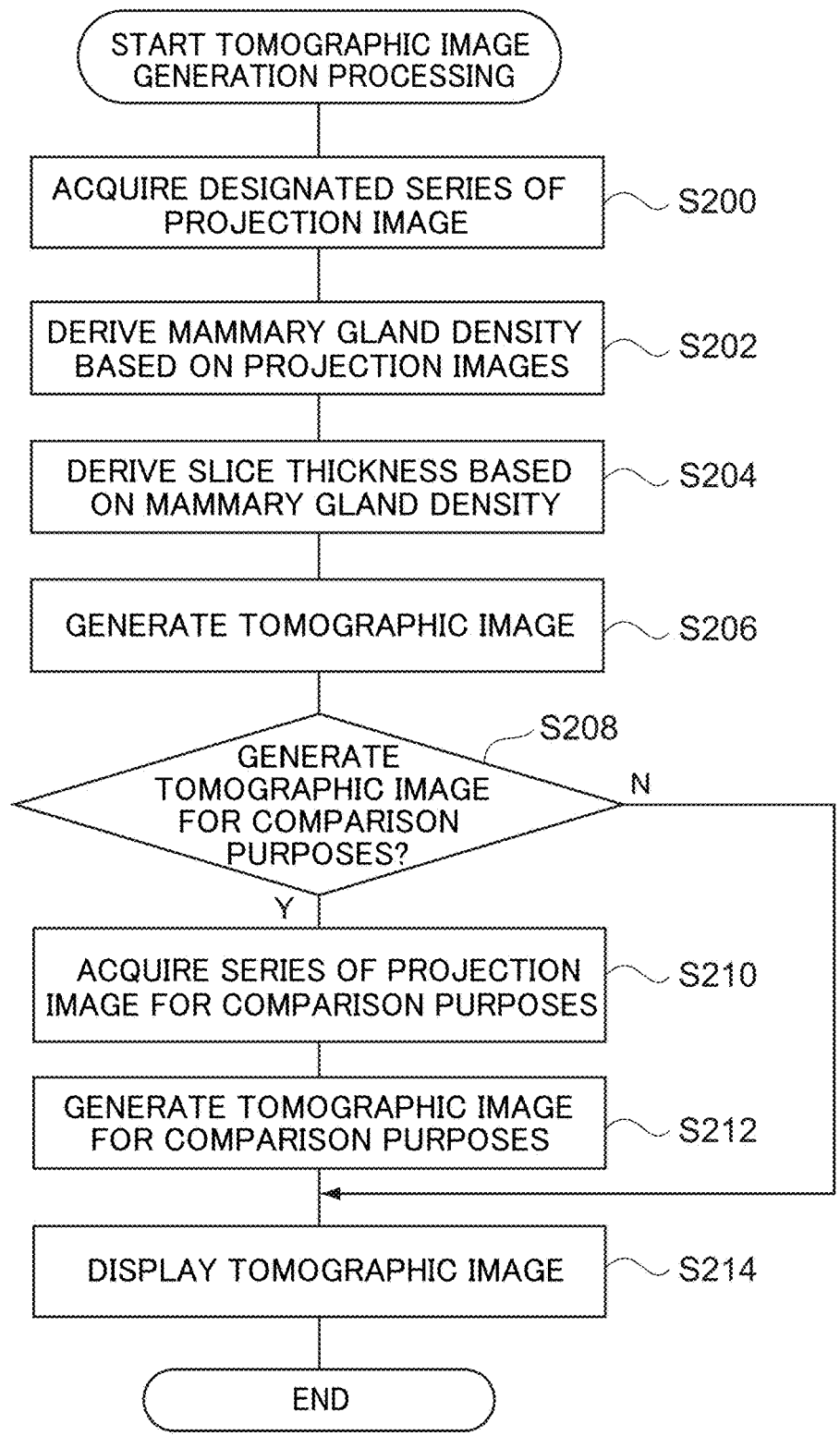
FIG. 13 is a flowchart illustrating a flow of tomographic image generation processing executed by a console of a fourth exemplary embodiment.

FIG. 13 is a flowchart illustrating a flow of tomographic image generation processing executed by the controller 60 of the radiographic image reader 14 of the present exemplary embodiment. A specific example is explained below of a case in which a user performs a diagnosis on the right breast of a subject by comparing a tomographic image of the right breast with a tomographic image of the left breast of the same subject imaged at the same session.

At step S200, the controller 60 selects, from plural sets of projection image series, a projection image series designated by the user through the operation section 72, and acquires the designated projection image series either by reading from the storage section 62, or by receiving from an external device, such as the console 12. In a specific example, the controller 60 first acquires a projection image series of the right breast of the subject to be diagnosed as designated by the user.

At the next step S202, similarly to step S102 of the tomographic image generation processing of the first exemplary embodiment (see FIG. 4), the controller 60 derives the mammary gland density Gd of the breast of the imaging subject based on the acquired projection images.

At the next step S204, similarly to at step S104 of the tomographic image generation processing of the first exemplary embodiment (see FIG. 4), the controller 60 derives the slice thickness Td based on the mammary gland density Gd derived at step S202.

At the next step S206, based on the projection image series acquired at step S200, the controller 60 generates a tomographic image at the derived slice thickness Td using the tomographic image generation method described above.

At the next step S208, the controller 60 determines whether or not to generate a tomographic image for comparison purposes. Negative determination is made in cases in which, unlike in this specific example, the user is not going to perform a comparison of respective tomographic images, and processing proceeds to step S214. However, affirmative determination is made in cases in which, as in this specific example, the user is going to perform a comparison of respective tomographic images, and processing proceeds to step S210.

At step S210, the controller 60 acquires a projection image series for comparison purposes designated by the user through the operation section 72 by reading from the storage section 62, or by receiving from an external device, such as the console 12. In this specific example, the controller 60 acquires a projection image series for the left breast of the subject being screened as designated by the user.

At the next step S212, based on the projection image series for comparison purposes acquired at step S210, the controller 60 generates a tomographic image for comparison purposes at the slice thickness Td derived at step S206 using the tomographic image generation method described above.

At the next step S214, the controller 60 controls the display section 68 so as to display the generated tomographic image or images, and then ends the present tomographic image generation processing. Note that in cases in which a tomographic image for comparison has not been generated, the controller 60 causes the display section 68 to display only the tomographic image generated at step S206. However, in cases in which a tomographic image for comparison purposes has been generated, the controller 60 causes the display section 68 to display the tomographic image generated at step S206, together with the tomographic image for comparison purposes generated at step S212.

In the present exemplary embodiment, the controller 60 of the radiographic image reader 14 accordingly: derives the mammary gland density Gd of the breast based on the projection image series designated by the user; derives the slice thickness Td corresponding to the mammary gland density Gd based on the information 43 or 43A expressing a predetermined correspondence relationship between mammary gland density and slice thickness such that the slice thickness Td is thinner the higher the mammary gland density Gd; and, based on the projection images, generates a tomographic image at the slice thickness Td. The controller 60 moreover generates a tomographic image for comparison purposes at the slice thickness Td based on the projection image series for comparison purposes.

Thus, similarly to in each of the above exemplary embodiments, the radiographic image reader 14 of the present exemplary embodiment is capable of obtaining tomographic images having high visibility of objects of interest.

Moreover, in the radiographic image reader 14 of the present exemplary embodiment, due to the slice thickness Td being the same for the tomographic image based on the projection image series in the selected set and for the tomographic image for comparison purposes based on the projection image series for comparison purposes, the user is more easily able to compare the respective tomographic images, and is more easily able to perform diagnosis.

Although explanation has been given of a case in which there are two sets of projection image series, and two tomographic images are generated, these being the tomographic image of the breast for diagnosis and the tomographic image of the breast for comparison purposes, plural tomographic images of the breast may be generated for comparison purposes. For example, as a tomographic image of a breast for comparison purposes, a tomographic image may be generated for each series of projection images that have been imaged at different sessions. In such cases, steps S208 to S212 of the tomographic image generation processing should be repeated according to the number of tomographic images to be generated (the number of tomographic images of the breast for comparison purposes).

Fifth Exemplary Embodiment

Explanation follows regarding a fifth exemplary embodiment. Components similar to the radiography imaging system 1 according to the above exemplary embodiments are allocated the same reference numerals, and detailed explanation thereof is omitted.

Configuration of the radiography imaging system 1 is similar to that of the radiography imaging system 1 of the first exemplary embodiment (see FIG. 1 to FIG. 3), and so explanation thereof is omitted. In the radiography imaging system 1 of the present exemplary embodiment, similarly to in the fourth exemplary embodiment, the radiographic image reader 14 functions as a tomographic image generation device of the present disclosure.

In the radiography imaging system 1 of the above exemplary embodiments, explanation has been given of cases in which the slice thickness Td is derived based on the mammary gland density Gd derived based on the projection images. However, in cases in which there is a clear diagnostic objective, such as in cases in which diagnosis of calcification is being performed or cases in which diagnosis of a tumor is being performed, it is desirable to generate a tomographic image at a slice thickness Td according to the diagnostic objective irrespective of the mammary gland density Gd. Therefore, in cases in which a diagnostic objective has been received, the radiography imaging system 1 of the present exemplary embodiment derives a slice thickness Td according to the diagnostic objective. Thus, since part of the tomographic image generation processing performed by the controller 60 of the radiographic image reader 14 in the present exemplary embodiment differs from the tomographic image generation processing performed by the controller 40 of the console 12 of the first exemplary embodiment (see FIG. 4), explanation follows regarding differing processing.

Figure 14:
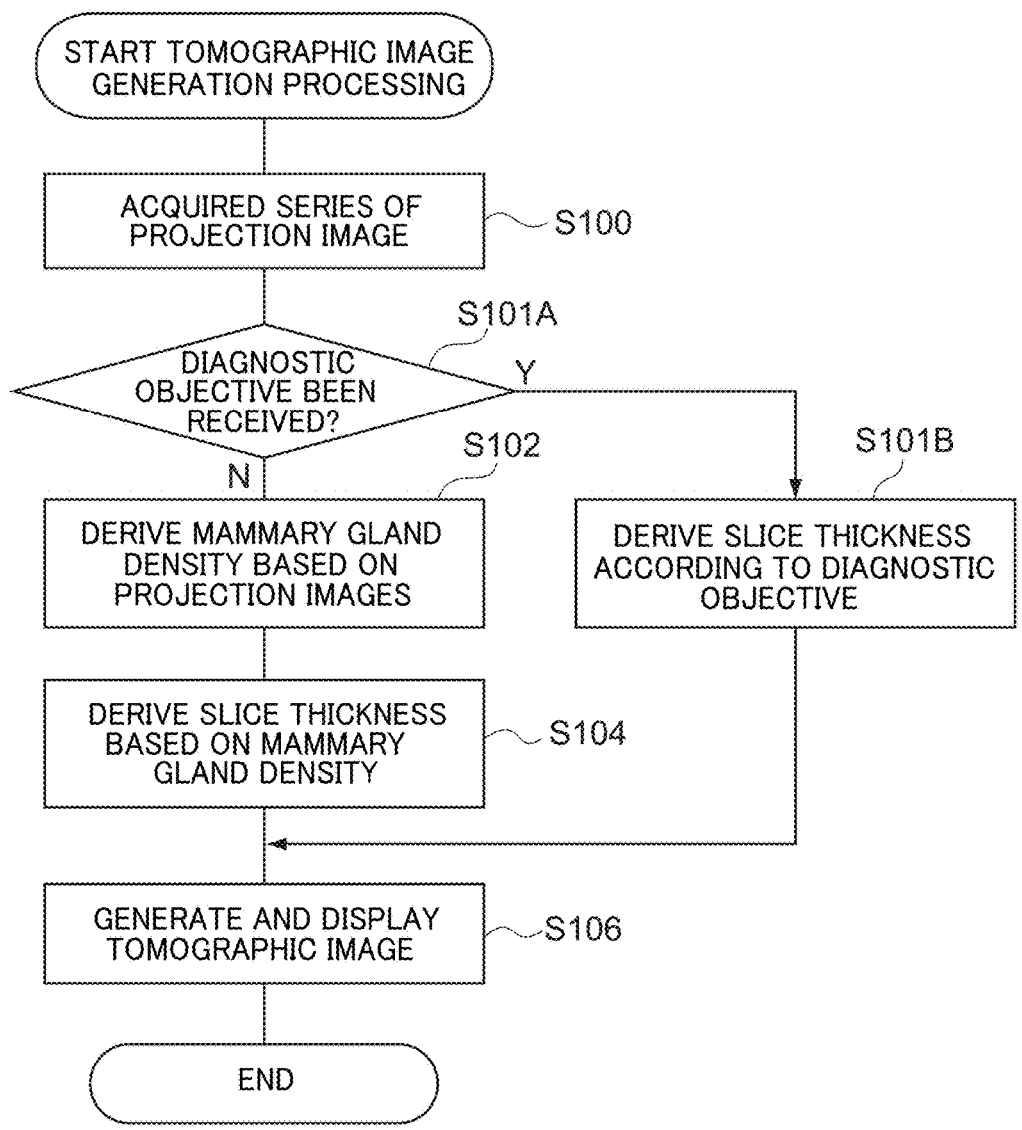
FIG. 14 is a flowchart illustrating a flow of tomographic image generation processing executed by a console of a fifth exemplary embodiment.

In the tomographic image generation processing executed by the controller 60 of the radiographic image reader 14 in the present exemplary embodiment, as illustrated in FIG. 14, step S101A is executed after step S100 in the tomographic image generation processing of the first exemplary embodiment (see FIG. 4), step S101B is executed in cases in which affirmative determination is made at step S101A, and processing is otherwise similar to that of the first exemplary embodiment.

At step S101A, the controller 60 determines whether or not a diagnostic objective has been received. The controller 60 determines that a diagnostic objective has been received in cases in which the operation input detection section 70 has detected a diagnostic objective input by the user using the operation section 72. For example, negative determination is made in cases in which a diagnostic objective has not been received, such as when the operation input detection section 70 has not detected input of a diagnostic objective even after a specific period of time has elapsed, and processing proceeds to step S102.

Affirmative determination is made when a diagnostic objective has been received, and processing proceeds to step S101B. At step S101B, the controller 60 derives the slice thickness Td according to the diagnostic objective, and then processing proceeds to step S106. There is no particular limitation to the method of deriving the slice thickness Td according to diagnostic objective. For example, information representing a correspondence relationship between a diagnostic objective, such as for diagnosing calcification or a tumor, and slice thickness Td, may be acquired in advance and stored in the storage section 62 or the like, and then the slice thickness Td derived based on information expressing the correspondence relationship between diagnostic objective, such as a follow-up observation of calcification or a tumor, and slice thickness Td read from the storage section 62 or the like.

The controller 60 of the radiographic image reader 14 in the present exemplary embodiment accordingly: acquires a projection image series; and, in cases in which a diagnostic objective has not been received; derives the mammary gland density Gd of the breast based on the projection image series; and derives the slice thickness Td corresponding to the mammary gland density Gd based on the information 43 or 43A expressing a predetermined correspondence relationship between mammary gland density and slice thickness such that the slice thickness Td is thinner the higher the mammary gland density Gd; and, based on the projection images, generates a tomographic image at the slice thickness Td. Moreover, in cases in which a diagnostic objective has been received, based on the projection image series, the controller 60 generates a tomographic image at the slice thickness Td according to the diagnostic objective.

The radiographic image reader 14 of the present exemplary embodiment accordingly, similarly to in the above exemplary embodiments, may also obtain a tomographic image having high visibility of objects of interest.

Further, in the radiographic image reader 14 of the present exemplary embodiment, due to the tomographic image being generated at the slice thickness Td according to the diagnostic objective in cases in which there is a clear diagnostic objective, a tomographic image according to the diagnostic objective may be generated in which viewing of calcification, a tumor, or the like is facilitated.

Note that although in the present exemplary embodiment it is only the tomographic image at the slice thickness Td derived according to the diagnostic objective that is generated when a diagnostic objective has been received, there is no limitation thereto, and a tomographic image may also be generated at a slice thickness Td derived according to the mammary gland density Gd. In such cases, the processing of each step of step S101B and steps S102 to S104 of the tomographic image generation processing illustrated in FIG. 14 may be executed.

Moreover, although explanation has been given of cases in the present exemplary embodiment in which the slice thickness Td is derived according to the diagnostic objective that was input by the user in order to facilitate viewing of calcification or a tumor, the method of deriving the slice thickness Td is not limited thereto.

For example, in cases in which information has been received related to the object of interest (such as calcification or a tumor) to be observed in the tomographic image to be generated (including for screening and diagnosis), in response to the received information, the controller 60 may derive a slice thickness Td according to the object of interest expressed in the received information. In such cases, the controller 60 may acquire in advance information expressing a correspondence relationship between slice thickness Td and the type, size, and the like of objects of interest, and store this information in the storage section 62 or the like. The controller 60 may cause the display section 68 to display some or all of the acquired projection image series, detect an object of interest designated by a user on the projection images being displayed, and derive a slice thickness Td according to the type, size, and the like of the object of interest obtained by image analysis or the like on the projection images.

As described above, in cases in which the position of an object of interest (position in a radiographic image) may be identified in projection images or the like, a tomographic image may be generated for a region containing the object of interest at a slice thickness Td according to the type, size, or the like of the object of interest, and for other regions, a tomographic image may be generated at a slice thickness Td according to the mammary gland density Gd.

As explained above, the controller 40 of the console 12 of the first to the third exemplary embodiments, and the controller 60 of the radiographic image reader 14 of the fourth and fifth exemplary embodiments, acquire plural projection images obtained by radiating radiation onto the breast in sequence from plural radiation angles, and imaging at each of the radiation angles. The controller 40 and the controller 60 also acquire the mammary gland density Gd of the breast. The controller 40 and the controller 60 derive a slice thickness Td so as to be thinner the higher the acquired mammary gland density Gd. Then, the controller 40 and the controller 60 generate a tomographic image at the derived slice thickness Td based on plural acquired projection images.

Due to generating a tomographic image at an appropriate slice thickness Td according to the mammary gland density Gd of the breast imaging subject, each of the above exemplary embodiments is accordingly able to obtain a tomographic image having high visibility of objects of interest. Due to being able to derive an appropriate slice thickness Td depending on the mammary gland density Gd, a tomographic image having an appropriate number of slices may be generated, and hence the time required for generating the tomographic image may also be made appropriate.

Although explanation has been given of cases in which the controller 40 of the console 12 in the first to the third exemplary embodiments, and the controller 60 of the radiographic image reader 14 in the fourth and fifth exemplary embodiments, function as the projection image acquisition section, the mammary gland density acquisition section, the derivation section, and the generation section of the present disclosure, the functions of each of the sections of the present disclosure may be provided in either the controller 40 or the controller 60.

There are no particular limitations to the radiation R in each of the above exemplary embodiments, and X-rays, gamma rays and the like may be employed therefor.

The configuration and operation of the radiography imaging system 1, the radiographic imaging device 10, the console 12, the radiographic image reader 14, and the like explained in each of the above exemplary embodiments are merely examples thereof, and obviously may be modified according to circumstances within a range not departing from the spirit of the present disclosure.

What is claimed is:

1. A tomographic image generation device comprising a memory and a processor coupled with the memory, the processor configured to:
    acquire a plurality of projection images obtained by radiating radiation onto a breast in sequence from a plurality of radiation angles and by performing imaging at each of the plurality of radiation angles;
    acquire a mammary gland density of the breast;
    determine a slice thickness based on the acquired mammary gland density of the breast such that the slice thickness decreases as the acquired mammary gland density increases; and
    generate a tomographic image at the derived slice thickness based on the plurality of acquired projection images, such that calcifications and/or tumors could appear under a mammary gland in the tomographic image.

2. The tomographic image generation device of claim 1, wherein the process is configured to derive the mammary gland density based on the plurality of acquired projection images.

3. The tomographic image generation device of claim 1, wherein the processor is configured to acquire, as the mammary gland density, a mammary gland density classification corresponding to a mammary gland density of the breast.

4. The tomographic image generation device of claim 1, wherein the processor is configured to:
    receive information related to mammary gland density; and
    acquire a mammary gland density based on the received information related to mammary gland density.

5. The tomographic image generation device of claim 1, wherein:
    the processor is configured to derive a predetermined first thickness as the slice thickness irrespective of the acquired mammary gland density, either in cases in which the acquired mammary gland density is a first threshold value or greater, or in cases in which the acquired mammary gland density exceeds the first threshold value.

6. The tomographic image generation device of claim 5, wherein the first thickness is determined according to a predetermined size of calcification.

7. The tomographic image generation device of claim 5, wherein the first thickness is about 0.1 mm.

8. The tomographic image generation device of claim 5, wherein the processor is configured to derive a predetermined second thickness that is larger than the first thickness as the slice thickness irrespective of the acquired mammary gland density, either in cases in which the acquired mammary gland density is, or is less than, a second threshold value that is smaller than the first threshold value, or in cases in which the acquired mammary gland density is less than the second threshold value.

9. The tomographic image generation device of claim 8, wherein the second thickness is determined according to a predetermined size of tumor.

10. The tomographic image generation device of claim 8, wherein the second thickness is about 4 mm.

11. The tomographic image generation device of claim 1, wherein the processor is configured to:
    acquire a plurality of sets of the plurality of projection images for the breast of a same subject;
    acquire a mammary gland density based on a set of the plurality of projection images selected from the plurality of sets; and
    generate a tomographic image for each of the sets at the derived slice thickness.

12. The tomographic image generation device of claim 11, wherein the plurality of sets of the plurality of projection images include at least one of a plurality of sets of a plurality of projection images corresponding respectively to each of left and right breasts of the same subject, or a plurality of sets of a plurality of projection images of the same breast of the subject imaged at different sessions.

13. The tomographic image generation device of claim 1, wherein the processor is configured to:
    receive information that is one set of information among first information related to a diagnostic objective of diagnosis to be performed using the tomographic image, or second information related to an object of interest to be observed in the tomographic image; and
    derive a predetermined slice thickness according to received information irrespective of mammary gland density in cases in which one set of the first or second information has been received.

14. The tomographic image generation device of claim 1, wherein the processor is configured to derive the slice thickness based on information expressing a correspondence relationship between the mammary gland density and the slice thickness.

15. A radiography imaging system comprising:
- a radiographic imaging device configured to image a plurality of projection images obtained by radiating radiation onto a breast in sequence from a plurality of radiation angles and imaging at each of the plurality of radiation angles; and
- the tomographic image generation device of claim 1, configured to acquire the plurality of projection images that have been imaged by the radiographic imaging device and to generate a tomographic image based on the acquired plurality of projection images.

16. A tomographic image generation method comprising:
- acquiring a plurality of projection images obtained by radiating radiation onto a breast in sequence from a plurality of radiation angles and by performing imaging at each of the plurality of radiation angles;
- acquiring a mammary gland density of the breast;
- determining a slice thickness based on the acquired mammary gland density of the breast such that the slice thickness decreases as the acquired mammary gland density increases; and
- based on the acquired plurality of projection images, generating a tomographic image at the derived slice thickness, such that calcifications and/or tumors could appear under a mammary gland in the tomographic image.

17. A non-transitory storage medium storing a program that is executable to cause a computer to perform tomographic image generation processing, the tomographic image generation processing comprising:
- acquiring a plurality of projection images obtained by radiating radiation onto a breast in sequence from a plurality of radiation angles and by performing imaging at each of the plurality of radiation angles;
- acquiring a mammary gland density of the breast;
- determining a slice thickness based on the acquired mammary gland density of the breast such that the slice thickness decreases as the acquired mammary gland density increases; and
- based on the acquired plurality of projection images, generating a tomographic image at the derived slice thickness, such that calcifications and/or tumors could appear under a mammary gland in the tomographic image.

18. The tomographic image generation device of claim 14, wherein the information expressing a correspondence relationship between the mammary gland density and the slice thickness comprises a linear function.

19. The tomographic image generation device of claim 14, wherein the information expressing a correspondence relationship between the mammary gland density and the slice thickness comprises an exponential function.

20. The tomographic image generation device of claim 14, wherein the information expressing a correspondence relationship between the mammary gland density and the slice thickness comprises a graph plotting discrete values of the slice thickness against the mammary gland density.

* * * * *